United States Patent [19]

Durairaj

[11] Patent Number: 4,945,169
[45] Date of Patent: Jul. 31, 1990

[54] BIS-MALEIMIDE COMPOUNDS CONTAINING SULFONATE LINKAGES

[75] Inventor: Bojayan Durairaj, Pittsburgh, Pa.

[73] Assignee: Indspec Chemical Corporation, Pittsburgh, Pa.

[21] Appl. No.: 215,555

[22] Filed: Jul. 6, 1988

[51] Int. Cl.$^5$ .................. C07D 403/10; C07D 403/12
[52] U.S. Cl. ..................................... 548/521; 548/522
[58] Field of Search ......................................... 548/521

[56] References Cited

U.S. PATENT DOCUMENTS 3,839,358 10/1974 Bargain .............................. 548/521

Primary Examiner—Christine M. Nucker
Assistant Examiner—Frederick F. Tsung
Attorney, Agent, or Firm—Herbert J. Zeh, Jr.; Arnold B. Silverman

[57] ABSTRACT

Novel homo bis-maleimide compounds containing sulfonate linkages are made by reacting an aromatic disulfonyl halide with m- or p-hydroxy phenyl maleimide and have the following formula:

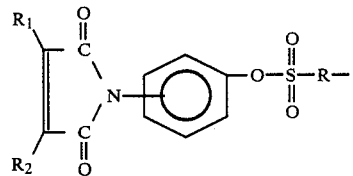

-continued

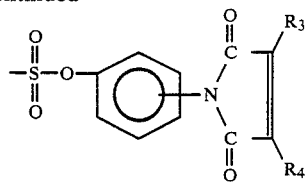

Similarly, co-bis-maleimides are made by reaching an aromatic disulfonyl halide, aromatic dihydroxy compound and m or p hydroxy phenyl maleimide having the structural formula:

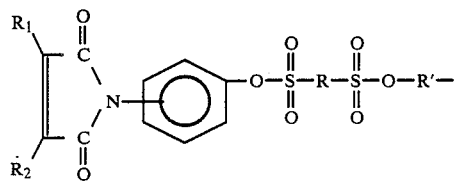

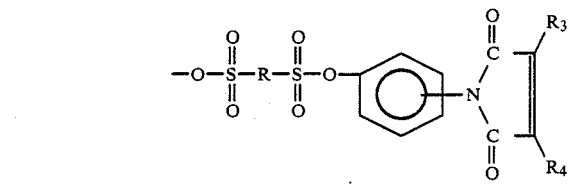

Herein R and R' are the same or different and are divalent radicals selected from the group consisting of meta arylene, para arylene, naphthalene and radicals of the formula A—A and A—Z—A wherein A is selected from the group consisting of meta arylene, para arylene and naphthalene and Z is selected from the group consisting of meta arylene, para arylene, naphthalene, carbonyl, sulfone, sulfide, sulfonyl, sulfonate, sulfoxide, ether, methylene, isopropyl, oxygen, alkyl, —CH═CH— and —C≡C— and $R_1$, $R_2$, $R_3$ and $R_4$ are the same or different and are selected from the group consisting of hydrogen, an alkyl group having from 1 to about 4 carbon atoms and a halogen.

8 Claims, No Drawings

BIS-MALEIMIDE COMPOUNDS CONTAINING SULFONATE LINKAGES

BACKGROUND OF THE INVENTION

1. Field of the Invention.

This invention relates to sulfonate-containing bis-maleimide resins. More particularly, this relates to sulfonate containing bis-maleimides prepared by reacting an aromatic disulfonyl chloride and m- or p-hydroxy phenyl maleimide in an organic solvent in the presence of a base. These bis-maleimide resins can be used in the production of fiber or fabric reinforced composites or laminates.

2. Description of the Prior Art.

High performance composites can be made by embedding various types of fibers or fabrics in a resin matrix. The matrix resins usually employed are an epoxy, phenolic, polyester and poly(sulfones). In addition to these resins, bis-maleimides have also been used to develop high performance composites with fibers or fabrics such as carbon, graphite and glass for certain applications. Besides high reactivity, bis-maleimides undergo addition type polymerization reactions producing networks without any volatile by-products. Accordingly, void-free composite materials for high temperature applications can be easily fabricated from these bis-maleimides.

Bis-maleimides containing groups like sulfone, ether, methylene, isopropylene, sulfide, etc., in the main chain are documented and known for thermal stability. Similarly, polymers containing sulfonate linkages show thermal stability and process ability. Though thermally stable co-poly (ester-sulfonates) with good mechanical properties are known, bis-maleimides containing sulfonate linkages are not known. So, bis-maleimides containing sulfonate groups would be expected to yield the combining properties of thermal stability and processability.

The primary object of the present invention is to develop new sulfonate containing bis-maleimides that can be used as a matrix resin for the fabrication of glass, graphite or carbon fiber or cloth composites and adhesives.

SUMMARY OF THE INVENTION

In accordance with the invention, new bis-maleimides containing sulfonate linkages are produced by reacting aromatic disulfonyl chloride and hydroxy phenyl maleimide in the presence of triethylamine in methylene chloride reaction solvent.

Further, according to the invention, thermosetting homo-bis-maleimide resins are produced having the following formula:

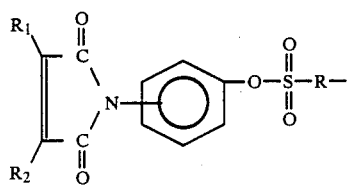

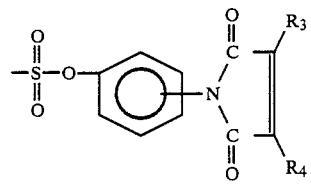

Wherein $R_1$, $R_2$, $R_3$ and $R_4$, which may be the same or different, each represents a hydrogen atom, a lower alkyl group (e.g., methyl, ethyl, propyl, allyl, etc.) or a halogen atom (such as chlorine or bromine) and wherein R is a divalent radical selected from the group consisting of meta arylene, para arylene, naphthalene and radicals of the forumla A-A and A-Z-A wherein A is selected from the group consisting of meta arylene, para arylene and naphthalene and Z is selected from the group consisting of meta arylene, para arylene, naphthalene, carbonyl, sulfone, sulfide, sulfonyl, sulfonate, sulfoxide, ether, methylene, isopropyl, oxygen, alkyl, —CH=CH— and —C≡C—.

Further, according to the invention, co-reaction of aromatic disulfonyl chloride, dihydroxy compound and m- or p-hydroxy phenyl maleimide is carried out in the presence of methylene chloride solvent containing hydrogen halide acceptor and having the general formula:

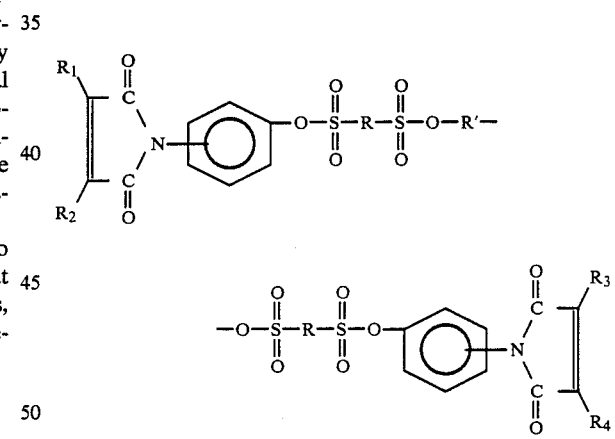

wherein R and $R^1$ are the same or different and are divalent radicals selected from the group consisting of meta arylene, para arylene, naphthalene and radicals of the forumla A-A and A-Z-A wherein A is selected from the group consisting of meta arylene, para arylene and naphthalene and Z is selected from the group consisting of meta arylene, para arylene, naphthalene, carbonyl, sulfone, sulfide, sulfonyl, sulfonate, sulfoxide, ether, methylene, isopropyl, alkyl, —CH=CH— and —C≡C— and $R_1$, $R_2$, $R_3$ and $R_4$ are the same or different and are selected from the group consisting of hydrogen, an alkyl group having from 1 to about 4 carbon atoms and a halogen.

DESCRIPTION OF PREFERRED EMBODIMENTS

The conversion of this invention can be represented where R, $R_1$, $R_2$, $R_3$ and $R_4$ have the same meaning as is stated above and X is a halogen, as follows:

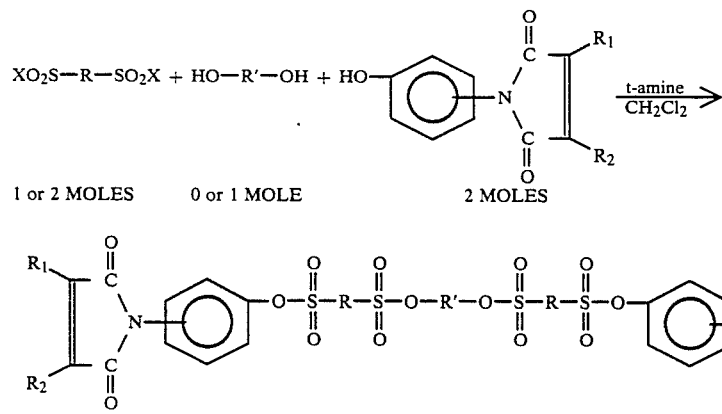

1 or 2 MOLES     0 or 1 MOLE     2 MOLES

In the above conversion, homo-bis-maleimide can be formed in the absence of any dihydroxy compound and co-bis-maleimide can be produced following the above reaction.

Examples of a suitable aromatic disulfonyl halide starting material ($XO_2S$-A-$SO_2X$) that can be applied according to the invention include:
o-, m- and p-benzene disulfonyl chloride
1-chloro-2,4-benzene disulfonyl chloride
1-methyl-2,4-benzene disulfonyl chloride
1-methoxy-2,4-benzene disulfonyl chloride
2,2'-biphenyl disulfonyl chloride
3,3'-biphenyl disulfonyl chloride
4,4'-biphenyl disulfonyl chloride
4,4'-dimethyl-3,3'-diphenyl sulfonyl chloride
4,4'-diphenyl methane disulfonyl chloride
2,2-bis-(4-phenyl sulfonyl chloride)-propane
4,4'-phenyl ether disulfonyl chloride
4,4'-biphenyl ether disulfonyl chloride
1,3-naphthalene disulfonyl chloride
2,6-naphthalene disulfonyl chloride
1,5-anthracene disulfonyl chloride
1,8-anthracene disulfonyl chloride The aromatic disulfonyl halides or chlorides can be prepared by the direct reaction of aromatic disulfonic acids or its salts with a chlorinating agent such as $PCl_5$, $PCl_3$, $POCl_3$, $SOCl_2$ by methods which are well known in the literature by the following reaction:

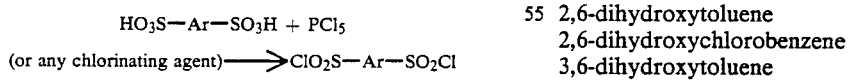

(or any chlorinating agent)

The preparation of m-benzenedisulfonyl chloride from sulfonic acid is, for example, described at pages 86–87 of *Preparative Methods of Polymer Chemistry* by Wayne R. Sorenson and Tod. W. Campbell, Interscience Publishers, Inc. (New York, 1961). The preparation of naphthalene-1,5-disulfonyl chloride from the disodium salt of naphthalene-1,5-disulfonic acid is described by P. D. Caesar, pages 693–695, Collective Volume 4 of *Organic Syntheses*, John Wiley & Sons, Inc. (New York, 1963), Norman Rabjohn, Editor-in-Chief.

Examples of diphenols that can be used for preparing co-bis-maleimides containing sulfonate linkage of this invention include:
bis-(4-hydroxyphenyl)-methane
bis-(4-hydroxy-3-methylphenyl)-methane
bis-(4-hydroxy-3,5-dichlorophenyl)-methane
bis-(4-hydroxy 3,5-dibromophenyl)-methane
bis-(4-hydroxy-3,5-difluorophenyl)-methane
bis-(4-hydroxyphenyl)-ketone
bis-(4-hydroxyphenyl)-sulfide
bis-(4-hydroxyphenyl)-sulfone
bis-(4-hydroxyphenyl)-ether
1,1-bis-(4-hydroxyphenyl)-ethane
2,2-bis-(4-hydroxyphenyl)-propane
2,2-bis-(4-hydroxyphenyl)-butane
2,2-bis-(4-hydroxyphenyl)-(4-nethyl)-pentane
2,2-bis-(4-hydrox-3-methylphenyl)-propane
2,2-bis-(4-hydroxy-3-chlorophenyl)-propane
2,2-bis-(4-hydroxy-3,5-dichlorophenyl)-propane
2,2-bis-(4-hydroxy-3,5-dibromophenyl)-propane
2,2-bis-(4-hydroxynaphthyl)-propane
bis-(4-hydroxyphenyl)-phenylmethane
bis-(4-hydroxyphenyl)-phenylmethylmethane
bis-(4-hydroxyphenyl)-diphenylmethane
bis-(4-hydroxyphenyl)-(4-methylphenyl)-methane
1,1-bis-(4-hydroxyphenyl)-2,2,2-trichloroethane
bis-(4-hydroxyphenyl)-(4-chlorophenyl)-methane
1,1-bis-(4-hydroxyphenyl)-cyclohexane
1,1-bis-(hydroxyphenyl)-(3-methylphenyl)-propane
bis-(4-hydroxyphenyl)-cyclohexylmethane
4,4'-dihydroxydiphenyl
2,2'-dihydroxydiphenyl
dihydroxynaphthalenes such as 2,6-dihydroxynaphthalene
hydroquinone
resorcinol
2,6-dihydroxytoluene
2,6-dihydroxychlorobenzene
3,6-dihydroxytoluene m- and p-hydroxy phenyl maleimides of this invention can be prepared in accordance with the disclosure contained in Oba et al., U.S. Pat. No. 4,289,699. By following the procedure described in U.S. Pat. No. 4,289,699, m- or p-hydroxy aniline was allowed to react with maleic anhydride in dimethyl formamide solvent to produce maleamic acid and, subsequently, cyclodehydrated using $H_2SO_4$ and $P_2O_5$ mixture to produce m- or p-hydroxy phenyl maleimide.

The organic solvent used for preparing the bis-maleimides may be an inert organic solvent to the disulfonyl chloride employed. Typical of such organic solvents include methylene chloride, tetrachlorethylene, tetrachloroethane, chloroform, benzene, toluene, xylene, carbon tetrachloride, o-dichlorobenzene, sulfolane, etc.

In the reaction of sulfonyl chloride with hydroxy compound, hydrogen chloride is produced as a by-product. In the presence of hydrogen halide acceptor in the reaction medium, hydrogen chloride forms a salt which can be easily separated by washing with water. The amount of hydrogen halide acceptor used will vary from 2 moles or greater, preferably in the range of 2.2–2.5 moles per mole of disulfonyl chloride employed. Examples of suitable hydrogen halide acceptors are tertiary amines which include pyridine, triethylamine, trimethylamine, tetramethylethylenediamine, N-methylpiperidine, triethylene diamine, hexamethylene tetramine and the like.

Reaction of disulfonylchloride with hydroxy compounds can be easily carried out by dissolving or dispersing disulfonyl chloride and hydroxy compounds in a suitable solvent, preferably methylene chloride, followed by adding an equivalent quantity or little excess of a base, preferably triethylamine, dropwise over a period of from 15 to 60 minutes, with thorough stirring. The addition of triethylamine or base can be done at a temperature of from +10 to 50° C. and preferably at room temperature. To ensure the completion of reaction, generally reaction mixture was stirred after the triethylamine addition for a period of 30 minutes to 3 hours, preferably 30 minutes to 1 hour at 40–45° C.

After the reaction, the bis-maleimide can be separated from the methylene chloride solution, after removing the salt by treatment with diluent HCl and water, by evaporating the methylene chloride or simply precipitate by pouring into a large quantity of nonsolvent diluent chosen from the group of hydrocarbons, preferably hexane. If precipitated, then the bis-maleimide has to be filtered, wash the precipitate with hexane and dried in vacuo at room temperature or higher temperature, preferably 70°–80° C.

Conventional reaction techniques and equipment can be employed.

The value and method of the process of this invention are demonstrated by the following examples:

EXAMPLE 1

To a stirred charge, in a 250 ml flask, of 2.75 g (0.01 mole) of m-benzene disulfonyl chloride, 35 ml of methylene chloride and 3.78 g (0.02 mole) of m-hydroxy phenyl maleimide was added 2.42 g (0.024 mole) of triethylamine during 15 minutes at room temperature. At the end of triethylamine addition, the reaction was continued at 40°–45° C. for additional 30 minutes. After completion of the reaction, the contents of the flask were transferred into a separatory funnel. The salt was extracted from the reaction solution with dilute hydrochloric acid and water. Bis-maleimide was precipitated by addition of the methylene chloride layer to a large excess of hexane. The precipitate was filtered, washed with hexane and dried in vacuo at 70°–80° C.

EXAMPLE 2

2.75 g of m-benzene disulphonyl chloride (0.01 mole), 3.78 g of p-hydroxy phenyl maleimide (0.02 mole) and 35 ml of methylene chloride were added into a three necked 250 ml flask provided with a stirrer, refluxing condenser and a dropping funnel. While stirring at room temperature, 2.42 g of triethylamine (0.024 mole) was added dropwise for 15 minutes through the addition funnel. At the end of triethylamine addition, the reaction was continued at 40°–45° C. for an additional 30 minutes. After the completion of reaction, the contents of the flask were transferred into a separatory funnel. The organic layer was extracted twice with dilute hydrochloric acid (1%) and then with equal volume of water to remove the salt. Bismaleimide was precipitated by the addition of the methylene chloride layer to a large excess of hexane. The precipitate was filtered and dried in vacuo at 70°–80° C.

EXAMPLE 3

2.75 g of m-benzene disulphonyl chloride (0.01 mole), 1.89 g of m-hydroxy phenyl maleimide (0.01 mole), 1.89 g of p-hydroxy phenyl maleimide (0.01 mole) and 35 ml of methylene chloride were successively brought into a three necked 250 ml flask fitted with a stirrer, reflux condenser and addition funnel. While stirring the contents of the flask at room temperature, 2.42 g of triethylamine (0.024 mole) was added dropwise within 15 minutes. At the end of the addition, external heat was applied by a warm water bath and gentle refluxing was continued for 30 minutes. After the completion of reaction, the contents of the reaction flask were transferred into a separatory funnel. The methylene chloride layer was extracted first with dilute hydrochloric acid (1%) and finally with equal volume of water. Bis-maleimide was isolated by the addition of the methylene chloride layer to a large excess of hexane. The precipitate was separated and dried in vacuo at 70°–80° C.

EXAMPLE 4

The reaction flask (250 ml) fitted with a stirrer, reflux condenser and dropping funnel was charged with 2.75 g of m-benzene disulphonyl chloride (0.01 mole), 0.55 g of resorcinol (0.005 mole), 1.89 g of p-hydroxy phenyl maleimide (0.01 mole) and 35 ml of methylene chloride. While stirring the contents of the flask at room temperature, 2.42 g of triethylamine (0.024 moles) was added dropwise within 15 minutes. At the end of the addition, external heat was applied by a warm water bath and gentle refluxing was continued for 30 minutes. After the completion of reaction, the contents of the flask were transferred into a separatory funnel. The methylene chloride layer was extracted first with dilute hydrochloric acid (1%) and finally with equal volume of water. Bis-maleimide was isolated by the addition of the methylene chloride layer to a large excess of hexane. The precipitate was separated and dried in vacuo at 70°–80° C.

What is claimed is:

1. Bis-maleimides containing sulfonate linkages of the formula:

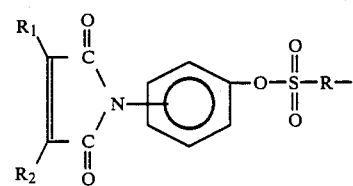

-continued

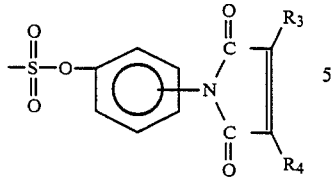

wherein R is a divalent radical selected from the group consisting of meta phenylene, para phenylene, naphthalene and radicals of the formula A—A and A—Z—A wherein A is selected from the group consisting of meta phenylene, para phenylene and naphthalene and Z is selected from the group consisting of meta phenylene, para phenylene, naphthalene oxygen, —CH=CH— and —C≡C—and $R_1$, $R_2$, $R_3$ and $R_4$ are the same or different and are selected from the group consisting of hydrogen, an alkyl group having from 1 to about 4 carbon atoms and a halogen.

2. Bis-maleimides containing sulfonate linkages of the formula:

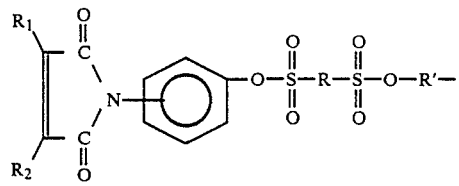

-continued

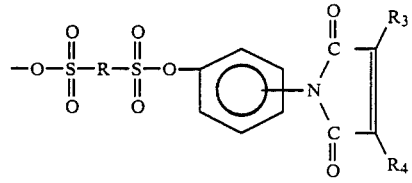

wherein R and R' are the same or different and are divalent radicals selected from the group consisting of meta phenylene, para phenylene, naphthalene and radicals of the formula A—A and A—Z—A wherein A is selected from the group consisting of meta phenylene, para phenylene and naphthalene and Z is selected from the group consisting of meta phenylene, para phenylene, naphthalene, oxygen, —CH=CH— and —C≡C— and $R_1$, $R_2$, $R_3$ and $R_4$ are the same or different and are selected from the group consisting of hydrogen, an alkyl group having from 1 to about 4 carbon atoms and a halogen.

3. The compound of claim 1 wherein R is meta phenylene.

4. The compound of claim 1 wherein R is para phenylene.

5. The compound of claim 1 wherein R is naphthalene.

6. The compound of claim 2 wherein R and R' are meta phenylene.

7. The compound of claim 2 wherein R and R' are para phenylene.

8. The compound of claim 2 wherein R and R' are naphthalene.

* * * * *